(12) United States Patent
Yin et al.

(10) Patent No.: US 8,524,216 B2
(45) Date of Patent: Sep. 3, 2013

(54) STERILIZING POLYMER AND METHOD OF PREPARATION THEREOF

(75) Inventors: Shengzhang Yin, Shandong (CN); Qiaoleng Wang, Shandong (CN); Zhiyong Zhang, Shandong (CN)

(73) Assignee: Qingdao Continent Pharmaceutical Co., Ltd. (CN)

( * ) Notice: Subject to any disclaimer, the term of this patent is extended or adjusted under 35 U.S.C. 154(b) by 166 days.

(21) Appl. No.: 13/058,713

(22) PCT Filed: Jun. 22, 2009

(86) PCT No.: PCT/CN2009/072370
§ 371 (c)(1),
(2), (4) Date: Feb. 11, 2011

(87) PCT Pub. No.: WO2010/020136
PCT Pub. Date: Feb. 25, 2010

(65) Prior Publication Data
US 2011/0135593 A1 Jun. 9, 2011

(30) Foreign Application Priority Data

Aug. 22, 2008 (CN) .......................... 2008 1 0147235

(51) Int. Cl.
*A61K 31/765* (2006.01)
*C08F 220/06* (2006.01)

(52) U.S. Cl.
USPC ..................................... 424/78.37; 526/317.1

(58) Field of Classification Search
USPC ..................................... 424/78.37; 526/317.1
See application file for complete search history.

(56) References Cited

FOREIGN PATENT DOCUMENTS

| | | |
|---|---|---|
| CN | 87108390 A | 9/1988 |
| CN | 1291895 A | 4/2001 |
| CN | 1875039 A | 12/2006 |
| IL | 145566 | 9/2001 |
| WO | WO 01/60874 A1 * | 8/2001 |

OTHER PUBLICATIONS

PCT International Search Report, Oct. 1, 2009, for Qingdao Continent Pharmaceutical Co. Ltd. et al., Int'l App'l No. PCT/CN2009/072370, filed Jun. 22, 2009.

* cited by examiner

*Primary Examiner* — Blessing Fubara
(74) *Attorney, Agent, or Firm* — Law Offices of Albert Wai-Kit Chan, PLLC

(57) ABSTRACT

The present invention provided a polymer and a method for preparing the polymer, wherein the polymer was a terpolymer having a molecular weight of more than 1000, and copolymerized by acrolein, acrylic acid, and low alkene-alkyl dibasic acid or low-alkene-alkyl polybasic acid.

14 Claims, No Drawings

STERILIZING POLYMER AND METHOD OF PREPARATION THEREOF

This application is the National Stage of Int'l App'l No. PCT/CN2009/072370, filed Jun. 22, 2009, which claims priority of Chinese Application No. 200810147235.8, filed Aug. 22, 2008. The entire contents and disclosures of the preceding applications are incorporated by reference into this application.

FIELD OF INVENTION

The invention provides an antimicrobial polymer and a method for preparing the polymer, wherein the polymer is a terpolymer having a molecular weight of more than 1000, and copolymerized by acrolein, acrylic acid, and low alkene-alkyl dibasic acid or low-alkene-alkyl polybasic acid.

BACKGROUND OF THE INVENTION

Research on the acrolin polymer was first seen in patent CN87108390 applied by Melrose Graham (Australia) in 1988. The patent introduced polyacrolein polymer with antimicrobial activities. The formation of polymer could eliminate the toxicity of low molecular weight and pungent odor of acrolin, while retaining the biological activity of acrolein. However, due to the extremely poor dissolubility, the application of polyacrolein was limited. In patent CN1875039, the method of heating and adding polyethylene glycol was used to promote the dissolubility of polyacrolein, but the dissolution was very time consuming and with poor stability. In patent AU-A-11686/95, it was mentioned that hydrogen peroxide could be used to oxidize partial acetal radical into carboxyl group to improve the stability. In patent CN1291895, acrylic acid and acrolein were copolymerized to improve the dissolubility, but the dissolubility would be decreased with the increase in the proportion of acrolein. In this patent, it was also mentioned to use surfactant and acidifier to improve the chemical stability of the polymer. In patent CN1347425 and CN1617733, polyoxyl, alcohol phenyl, polyalcohol and/or alkanol were added to improve the stability and bactericidal activity of poly (acrolein, acrylic acid). However, it had been found in some studies that, the biological activities were not improved when polyoxyl, alcohol phenyl, polyalcohol and/or alkanol were added. The original defect still existed, and this type of the polymers including the following repeating units:

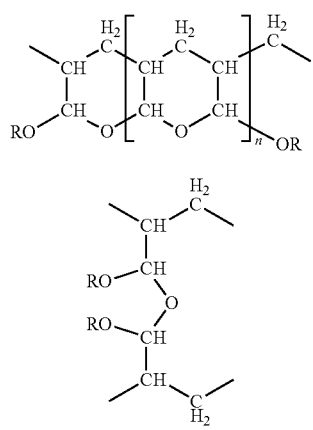

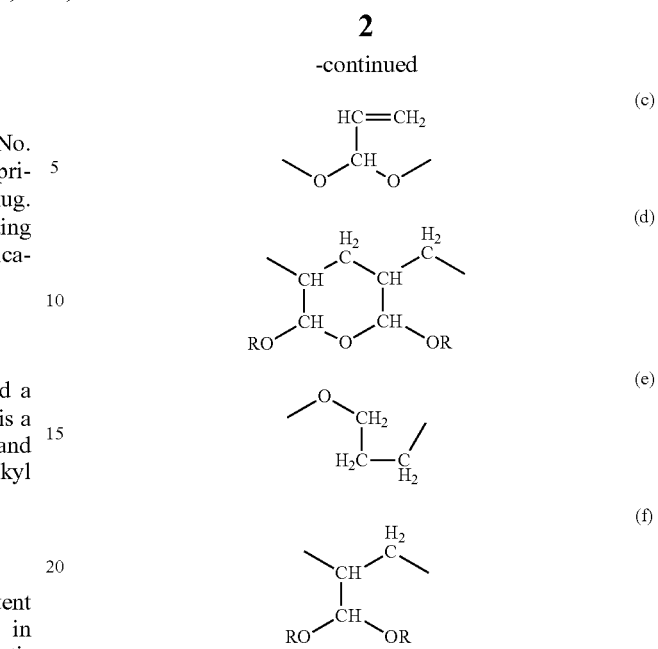

Wherein R is H, n is an integer ≥1.

SUMMARY OF THE INVENTION

The objective of this invention is to provide a new polymer and a preparing method to overcome the above defects.

In one embodiment, the invention provides a bactericidal polymer, which is a terpolymer having a molecular weight of 1000-10000 Daltons, and formed by copolymerizing of acrolein, acrylic acid, and low molecular weight alkene-alkyl dibasic acid or polybasic acid. Its structure comprises one or more repeating units. Examples of repeating units include the following structures A-E:

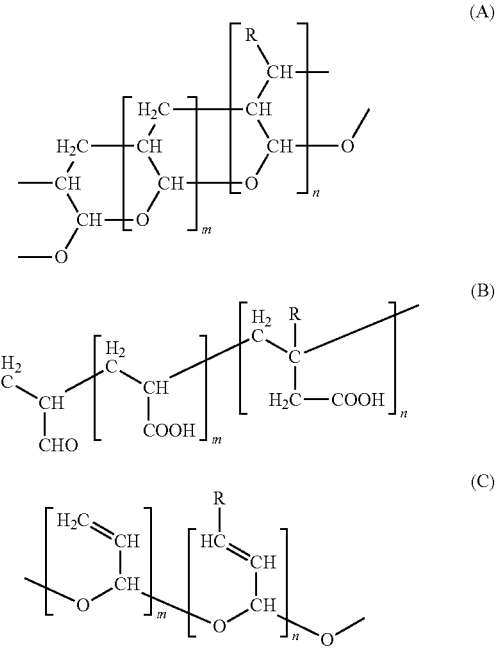

-continued

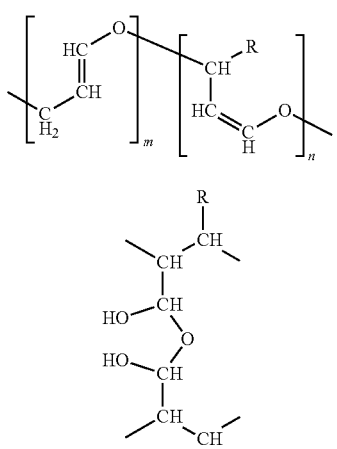

Wherein m and n are integers $\geq 1$, R is H or —$R_1$COOH, and $R_1$ is a $C_0$-$C_{10}$ alkyl group, alkenyl or polybasic alkyl group with double bonds. In another embodiment, $R_1$ could be $C_0$-$C_5$ alkyl group. In another embodiment, $R_1$ could be $C_0$-$C_2$ alkyl group, wherein R=(—$CH_2$COOH).

In one embodiment, the polymer content of carboxyl group is 0.15-7.5 mole/kg and molecular weight of the polymer is 1000-5000.

In one embodiment, the raw materials include: acrolein, acrylic acid and alkenyl polybasic acid, wherein the polybasic acid can be maleic acid, fumaric acid, trans-glutaconic acid or cis-glutaconic acid.

In one embodiment, the raw materials of this invention include acrylic acid, acrolein and cis (trans) maleic acid. In another embodiment, raw materials are acrylic acid, acrolein and fumaric acid. In one embodiment, the mole ratio range of acrylic acid:acrolein:fumaric acid is 1-100:1-100:1-100. In another embodiment, acrylic acid:acrolein:fumaric acid is 1-98:1-50:1-50. In another embodiment, acrylic acid:acrolein:fumaric acid is 40-90:10-50:1-10. In another embodiment, acrylic acid:acrolein:fumaric acid is 50-70:20-40:5-9, and in still yet embodiment, acrylic acid:acrolein:fumaric acid is 63:30:7.

The polymer of this invention can be prepared through the following steps:

Distilled acrylic acid, distilled acrolein, and fumaric acid were added into a three-port flask with absolute methanol and purged with nitrogen, benzoyl peroxide was added, and the solution was stirred and heated to reflux under nitrogen. The reacting solution became a brown viscous liquid, which was dried under vacuum to form acrylic acid-acrolein-fumaric acid copolymer.

The invention also includes the pharmaceutical compositions containing the invented polymer as the active ingredients and the pharmaceutically acceptable carrier. The polymer of this invention can be combined with other active ingredients as the synergist of antibacterial and anti-coccidiosis, as long as they are not antagonistic.

The pharmaceutical compositions of this invention can be formulated into any suitable dosage form, e.g.: oral preparation (such as tablet, capsules, oral liquid, suspension, pills and granules), local agents (such as ointment, solution and suppositories, etc). The pharmaceutical compositions of this invention can be prepared in accordance with the well known method in pharmaceutical field.

The carriers of pharmaceutical compositions in this invention are easily available in pharmaceutical field, including adhesives, lubricants, disintegrant, dispersion agents, solvents, diluents, stabilizers, suspending agents, flavoring agents etc., which are used in oral preparations and controlled release carriers for sustained-release or controlled release preparations; as well as matrix, thinners, lubricants, preservatives for local agents, etc.

Another objective of this invention is to provide this polymer in the preparations against bacterial and parasitic infections in animals and humans.

The dose of polymer in this invention can be properly adjusted according to therapeutic efficacy of in vivo bioavailability, metabolism and excretion rate of active ingredients, the age, sex, and disease stage of the patients. Therefore, the therapeutic dose can be a wide range of changes. Generally, the dose of the polymer can be adjusted according to the actual amounts of therapeutic ingredients or pharmaceutical compositions mentioned in this invention to reach the request of effective treatment, and complete the purpose of this invention to treat the infections. Effective dose can follow the guidance of a doctor or physician, as a single dose administration or in the form of several certain intervals or continuously administration.

The doses of the above active ingredients can be changed according to different formulae. However, if necessary, the above mentioned doses may be deviated, which is determined by the category and bodyweight of the subjects, individual pharmaceutical behavior, nature and severity of the disease, type of preparation and method of administration, as well as time and intervals of administration.

The invention increases the proportion of carboxy groups in the polymer to promote its dissolubility. Meanwhile, it has disclosed stronger bactericidal activity in vitro.

The following contrast experiments illustrate the beneficial effects of the invention:

I. Synthesis Experiments

Synthesis of control drug (mole ratio, acrolein:acrylic acid=70:30): 24.55 g freshly distilled acrolein and 72.92 g freshly distilled acrylic acid were added into a three-port flask with 210 ml absolute methanol, purged with nitrogen, 4.41 g benzoyl peroxide was added, and the solution was stirred and heated to reflux under nitrogen for 70 h. The reacting solution became a brown viscous liquid, which was dried under vacuum at 50-100° C. for 24 hours to form poly (acrolein-acrylic acid) named A1.

Synthesis of the invented drug (mole ratio, acrylic acid:acrolein:fumaric acid=63:30:7): 73.7 g freshly distilled acrolein, 198.8 g freshly distilled acrylic acid and 35.6 g fumaric acid were added into a three-port flask with 630 ml absolute methanol, purged with nitrogen, and 13.2 g benzoyl peroxide was added, and the solution was stirred and heated to reflux under nitrogen for 70 h. The reacting solution became a brown viscous liquid, which was dried under vacuum at 50-100° C. for 24 hours to form poly (acrolein, acrylic acid, fumaric acid) named A2.

II. Contrast Experiments of Dissolubility:

Weighed 2.40 g Poly (acrolein-acrylic acid) A1 and 2.4 g Poly (acrolein, acrylic acid, fumaric acid) A2 as abovementioned were added into 100 ml water respectively, heated to boiling, then observed the phenomena and determined pH values; then added sodium carbonate to adjust the solution to be transparent, and adjusted pH value to be acidic and alkaline groups, the corresponding acidic solutions were B1 and B2, and the alkaline solutions were C1 and C2. The dissolving results were shown in table 1.

TABLE 1

| Name | boiling without sodium carbonate | | added sodium carbonate | | |
|---|---|---|---|---|---|
| | Phenomena | PH | Phenomena | Adjust PH to | Adjust PH to |
| Poly (acrolein, acrylic acid) A1 | Only swelling after boiling for 24 h | | Turbid solution only after boiling for more than 20 h, transparent solution | 4.10 (B1) | 8.49 (C1) |
| Poly (acrolein, acrylic acid, fumaric acid) A2 | milky solution after boiling for 30 min | 2.25 | | 4.15 (B2) | 8.46 (C2) |

III. Contrast Experiments of Toxicity:

Experimental method: bodyweight 18-22 g white rats, half ♀ and half ♂, fasted for 12 h before the experiment, and water was provided freely. Ten white rats were divided into one group. Made polymer A1 and A2 into a 50% solution, and injected 5000 mg/kg bodyweight and 10000 mg/kg bodyweight through the white rats mouth into their stomachs separately. White rats in polymer A2 group injected 10000 mg/kg all died, so 6500 mg/kg bodyweight and 8000 mg/kg bodyweight were additionally administered. The white rats were observed for 14 days after administration, and the experimental results were shown in table 2.

TABLE 2

| polymer name | Dose (mg/kg body weight) | Dead number of white rats |
|---|---|---|
| Poly (acrolein, acrylic acid) A1 | 5000 | 1 |
| | 10000 | 3 |
| Poly (acrolein, acrylic acid, fumaric acid) A2 | 5000 | 1 |
| | 6500 | 1 |
| | 8000 | 3 |
| | 10000 | 10 |

IV. Contrast Experiments of Bactericidal Efficacy:
Experimental Method
1. Bacteria Cultivation Crossed the bacteria strains and inoculated onto MH solid culture medium then cultured for 24 h, picked single colony by a sterilized tip and inoculated into 3 ml MH broth culture medium, then placed into a 37° C. constant temperature incubator for 18 h.

2. Bacteria Count

Put 8 sterilized tubes (13×10 mm) on the tube shelf in order from 1 to 8. Added 9 ml sterilized MH broth medium in each tube, then added 1 ml of the above-mentioned bacteria solution into No. 1 tube, after mixing up, withdrew 1 ml and added into No. 2 test tube, then mixed up, withdrew 1 ml into No. 3 test tube, and diluted in order till the No. 8 test tube, took No. 5-8 test tube samples, withdrew 0.1 ml bacteria solution from each test tube and smeared onto the sterilized MH solid culture medium, and each sample was tested for 3 times. Placed the culture medium into a 37° C. constant temperature incubator and cultured for 18 hours. Chose appropriate culture dish to count the bacteria, and adopt mean value as the concentration of bacteria solution.

3. Determining Method

Preparation of standard bacteria solution: diluted the cultured and counted fresh bacteria solution with MH broth culture medium for later use.

Assay: took 10 sterilized test tubes (13×10 mm) and put onto the tube shelf in order from No. 1 to 10. Added 1.8 ml the above diluted bacterial solution into No. 1 test tube, and withdrew 1 ml into No. 2-8 tubes. Added 0.2 ml polymer sample into No. 1 test tube, and mixed up. Withdrew 1 ml solution from No. 1 test tube into the No. 2 test tube, and diluted the bacteria solutions from No. 2 to No. 10 test tubes, and discard 1 ml from the No. 10 test tube. Stopped up all the test tubes, cultured in a 37° C. incubator for 18 h, and observed the results.

*Staphylococcus aureus*: *Staphylococcus aureus* was isolated from chicken intestines in chicken farm, bacteria concentration was $1.7 \times 10^8$ cfu/ml, and the bactericidal efficacies were shown in table 3.

TABLE 3

| | Concentration (mg/ml) | | |
|---|---|---|---|
| Polymer name | 2.4000 | 1.2000 | 0.6000 |
| B1 | + | + | − |
| C1 | + | − | − |
| B2 | + | + | − |
| C2 | + | + | − |

+ efficient,
− inefficient

2) *Bacillus coli*: *Bacillus coli* was isolated from chicken intestines in chicken farm, bacteria concentration was $5 \times 10^6$ cfu/ml, and the bactericidal efficacies were shown in table 4.

TABLE 4

| | Concentration (mg/ml) | | |
|---|---|---|---|
| Polymer name | 2.4000 | 1.2000 | 0.6000 |
| B1 | + | + | − |
| C1 | − | − | − |
| B2 | + | + | − |
| C2 | − | − | − |

+ efficient,
− inefficient

3) *Bacillus aeruginosus*: *Bacillus aeruginosus* was standard bacteria strain at a concentration of $3.1 \times 10^5$ cfu/ml, and the bactericidal efficacies were shown in table 5.

TABLE 5

| | Concentration (mg/ml) | | |
|---|---|---|---|
| Polymer name | 2.4000 | 1.2000 | 0.6000 |
| B1 | + | + | − |
| C1 | + | − | − |
| B2 | + | + | − |
| C2 | + | − | − |

+ efficient,
− inefficient

4) *Salmonella*: *Salmonella* was isolated from chicken intestines in chicken farm, bacteria concentration was $3.4 \times 10^4$ cfu/ml, and the bactericidal efficacies were shown in table 6.

TABLE 6

| Polymer name | Concentration (mg/ml) | | |
|---|---|---|---|
| | 2.4000 | 1.2000 | 0.6000 |
| B1 | + | + | − |
| C1 | + | − | − |
| B2 | + | + | − |
| C2 | + | + | − |

+ efficient,
− inefficient

Experimental Conclusion:

As observed in table 1, the dissolubility of A2 was better than that of A1, which meant that biprotic acid was introduced in poly (acrolein, acrylic acid) greatly improved dissolubility of the polymer, and the stability of the polymer solution was also improved.

As observed in table 2, 3 rats died at dose of 10000 mg/kg bodyweight poly (acrolein, acrylic acid), so we inferred that the LD50 of poly (acrolein, acrylic acid) was no less than 10000 mg/kg bodyweight; 3 rats died at the dose of 8000 mg/kg bodyweight poly (acrolein, acrylic acid, fumaric acid), so its LD50 was between 8000 and 10000 mg/kg bodyweight. The toxicity of poly (acrolein, acrylic acid, fumaric acid) was higher than that of poly (acrolein, acrylic acid), but both of the polymers are all Low toxicity.

As observed in table 3, 4, 5 and 6, the results of bactericidal effects of the two polymers on *Staphylococcus aureus, Bacillus coli, Bacillus aeruginosus* and *Salmonella* indicated that the bactericidal effects of poly (acrolein, acrylic acid) and poly (acrolein, acrylic acid, fumaric acid) were equivalent under acidic conditions. However, in alkaline conditions, the bactericidal effects of poly (acrolein, acrylic acid, fumaric acid) were superior to that of poly (acrolein, acrylic acid). Moreover, the bactericidal effects of any polymer under acidic conditions were better than that under alkaline conditions.

Therapeutic experiments of the polymer of this invention to colibacillosis by artificial induction in broiler.

Test materials: The polymer of this invention was provided by Qingdao Continent Pharmaceutical Co., Ltd.; premixed origanum oil was bought from Weifang Jiajia Animal Husbandry R&D Co., Ltd., and Amikacin Sulfate was bought from Qilu Pharmaceutical Co., Ltd.

Test animals: 500 healthy AA+ chicks of 1 day old with similar primary bodyweight were chosen. The chicks were bred in the cages. Feeds were self-made powder, and the chicks could freely drink water and eat food under light for 24 h a day.

Infecting bacteria strain: Standard bacterial strain of Chick *E. coli* $O_{78}$ (CVCC4904) was bought from Control Institute of Veterinary Bioproducts and Pharmaceuticals, China.

Experiment: Animal groups: 350 healthy chicks of 21-day-old were randomized into 10 groups, with 35 chicks in each group.

Inoculation: 1 mL of *E. coli* solution was injected peritoneally for each chick to induce the disease. Drugs were administered when the chick fall ill.

TABLE 7

| Number | Drugs | pH value | Dose |
|---|---|---|---|
| Group 1 | Polymer A2 | 7.18 | 500 PPM administered with drinking water, 7 days continuously, twice daily |
| Group 2 | Polymer A2 | 7.18 | 400 PPM administered with drinking water, 7 days continuously, twice daily |
| Group 3 | Polymer A2 | 7.18 | 300 PPM administered with drinking water, 7 days continuously, twice daily |
| Group 4 | Polymer A2 | 7.18 | 200 PPM administered with drinking water, 7 days continuously, twice daily |
| Group 5 | Polymer A1 | 7.11 | 400PPML administered with drinking water, 7 days continuously, twice daily |
| Group 6 | Amikacin sulfate | | 210 PPM (as Amikacin) administered with drinking water, 7 days continuously, twice daily |
| Group 7 | Amikacin sulfate + polymer A2 | | 210 PPM (as Amikacin) + 300 PPM administered with drinking water, 7 days continuously, twice daily |
| Group 8 | Origanum oil | | 100 PPM mixed with feeds, 7 days continuously, twice daily |
| Group 9 | Infection group without administration | | |
| Group 10 | Non infection group without administration | | |

The chicks were inoculated by bacteria in test group when they were 24-day-old, different doses of drugs were added in drinking water after 12 h of inoculation for 7 days continuously, and twice daily.

Determined parameters: mortality, cured rate and effective rate of each drug group.

dead number: dead number was calculated by the number of died chicks which appeared typical symptoms of colibacillosis during the experiment and *E. coli* could be isolated from heart and liver of died chicks.

Cured number: Cured number was calculated based on the number of cured chicks which had recovered normal mental state after administration, with no decreased appetite, no dysentery etc.

Effective number: Effective number was calculated according to the number of living chick after the test including the cured or living chicks with clinical symptoms after administration.

Results: Comparison of treatment effects on *E. coli* of polymer A2, A1, amikacin sulfate, Amikacin Sulfate+polymer A2 and origanum oil were shown in table 8.

TABLE 8

| | Groups | | | | | | | | | | Dead chicks | Remain in chicks |
|---|---|---|---|---|---|---|---|---|---|---|---|---|
| | Group 1 | Group 2 | Group 3 | Group 4 | Group 5 | Group 6 | Group 7 | Group 8 | Group 9 | Group 10 | | |
| Drug name | Polymer A2 | Polymer A2 | Polymer A2 | Polymer A2 | Polymer A1 | Amikacin sulfate | Amikacin sulfate + PolymerA2 | Origanum cal | Infection group without admin- | Non infection group | | |

TABLE 8-continued

| | Group 1 | Group 2 | Group 3 | Group 4 | Group 5 | Group 6 | Group 7 | Group 8 | Group 9 | Group 10 administration | Dead chicks without drug | Remain in chicks |
|---|---|---|---|---|---|---|---|---|---|---|---|---|
| Chick num | 35 | 35 | 35 | 35 | 35 | 35 | 35 | 35 | 35 | 35 | | 350 |
| Died number during 0-12 h after inoculation | 1 | 3 | 1 | 3 | 1 | 4 | 1 | 4 | 0 | 0 | 18 | 332 |
| Chick number of administration | 34 | 32 | 34 | 32 | 34 | 31 | 34 | 31 | 35 | 35 | | 332 |
| Dead number at day 1 | 1 | 1 | 2 | 4 | 1 | 4 | 1 | 1 | 1 | 0 | 16 | 316 |
| Dead number at day 2 | 0 | 0 | 2 | 2 | 1 | 0 | 0 | 1 | 2 | 0 | 8 | 308 |
| Dead number at day 3 | 0 | 0 | 1 | 0 | 1 | 0 | 1 | 1 | 1 | 0 | 3 | 303 |
| Dead number at day 4 | 0 | 0 | 0 | 0 | 0 | 0 | 0 | 0 | 3 | 0 | 3 | 300 |
| Dead number at day 5 | 0 | 0 | 0 | 0 | 0 | 0 | 0 | 0 | 3 | 0 | 3 | 297 |
| Dead number at day 6 | 0 | 0 | 1 | 0 | 0 | 0 | 0 | 0 | 2 | 0 | 3 | 294 |
| Dead number at day 7 | 0 | 0 | 0 | 1 | 0 | 0 | 0 | 0 | 1 | 0 | 2 | 292 |
| Total dead number during administration (25-32 days) | 1 | 1 | 6 | 7 | 3 | 4 | 2 | 3 | 13 | 0 | 40 | |
| Dead number after withdrawal (33-42 days) | 0 | 0 | 1 | 0 | 3 | 2 | 0 | 3 | 2 | 0 | 11 | 281 |
| Total dead number after administration (26-42 days) | 1 | 1 | 7 | 7 | 6 | 6 | 2 | 6 | 15 | 0 | 51 | |
| remaining chick number | 33 | 31 | 27 | 25 | 28 | 25 | 32 | 25 | 20 | 35 | — | 281 |
| heating chick number | 28 | 25 | 20 | 16 | 25 | 18 | 26 | 17 | 11 | 35 | — | 221 |
| Sick chick number | 5 | 6 | 7 | 9 | 3 | 7 | 6 | 8 | 9 | 0 | — | 60 |
| Mortality (%) | 2.94 | 3.13 | 20.59 | 21.88 | 17.65 | 19.35 | 5.88 | 19.35 | 42.86 | 0 | — | |
| Cured rate (%) | 82.35 | 78.13 | 58.82 | 50.00 | 73.53 | 58.06 | 76.47 | 54.84 | 31.43 (self cured) | 0 | — | — |
| Effective rate (%) | 97.08 | 96.87 | 79.41 | 78.12 | 82.35 | 80.65 | 94.12 | 80.85 | — | — | — | — |

Note: mortality was Total dead number after administration/chick number before administration; cured rate was healthy chick number after administration/chick number before administration; effective rate was remaining chick number after administration/chick number before administration; Performance of sick chicks: depressed, loose and disordered feather, or pendulous wing, eyes unopened, poor appetite, emaciated, swollen articulation, not stand and weighed less than 1000 g.

Conclusion: as Shown in Table 8:

In table 8, group 2 and group 5 were the same dose of polymer A2 and polymer A1 and the results indicated that the mortality rates of group A2 and A1 were 3.13% and 17.65%, the cured rates were 78.13% and 73.53%, the effective rates were 96.87% and 82.35% respectively, and the effects of polymer A2 were superior to polymer A1.

In table 8, as observed in group 1, group 2, group 6 and group 8, when polymer A2 was administered at a dose more than 400 PPM, the mortality rate was far lower than that in groups administered 210 PPM amikacin sulfate and 100 PPM origanum oil, the cured rates and effective rates were also superior to those of amikacin sulfate and origanum oil groups, with significant difference; effects of polymer A2 in 300 PPM group were equivalent to that groups of amikacin sulfate in 210 PPM and origanum oil in 100 PPM, with no significant differences.

In table 8, comparison between group 6 and 7 indicated that polymer A2 had significant synergistic effects on amikacin sulfate in treating colibacillosis.

Implementation:

The following examples illustrated the invention but not limit the invention.

EXAMPLE 1

Control drug: (acrylic acid:acrolein (mol)=95:5): 3.25 g freshly distilled acrolein and 79.27 g freshly distilled acrylic acid were added into a three-port flask with 520 ml absolute methanol, purged with nitrogen, 4.74 g benzoyl peroxide was added, and the solution was stirred and heated to reflux under nitrogen for 50 h. The reaction solution became a yellowish viscous liquid, which was dried under vacuum at 50-100° C. for 24 hours to form poly (acrolein-acrylic acid) named A3.

Invented drug (acrylic acid:acrolein:fumaric acid (mol)= 90:5:5): 3.89 g freshly distilled acrolein, 90.08 g freshly distilled acrylic acid and 8.06 g fumaric acid were added into a three-port flask with 590 ml absolute methanol, purged with nitrogen, 5.04 g benzoyl peroxide was added, and the solution was stirred and heated to reflux under nitrogen for 50 h. The reaction solution became a yellowish viscous liquid, which was dried under vacuum at 50-100° C. for 24 hours to form Poly (acrolein, acrylic acid, fumaric acid) named A4.

Contrast Experiments of Dissolubility:

The results were shown in table 9.

TABLE 9

| Name | | Boiling without sodium carbonate | | added sodium carbonate | |
|---|---|---|---|---|---|
| | | Phenomena | PH | Phenomena | Adjust PH to | Adjust PH to |
| Poly (acrolein, acrylic acid) | A3 | Turbid solution after boiling | 2.10 | Transparent solution | 4.06 (B3) | 8.26 (C3) |
| Poly (acrolein, acrylic acid, fumaric acid) | A4 | Basically transparent solution after boiling | 2.15 | Transparent solution | 4.10 (B4) | 8.24 (C4) |

Contrast Experiments of Toxicity:

The results were shown in table 10:

TABLE 10

| Polymer name | Dose (mg/kg body weight) | Number of dead rats |
|---|---|---|
| Poly (acrolein, acrylic acid) A3 | 5000 | 0 |
| | 10000 | 1 |
| Poly (acrolein, acrylic acid, fumaric acid) A4 | 5000 | 0 |
| | 10000 | 1 |

Contrast Experiments of Bactericidal Efficacy:

1) *Staphylococcus aureus*: *Staphylococcus aureus* was isolated from chick intestines in the chicken farm, the concentration of bacteria was $2.5 \times 10^6$ cfu/ml, and the bactericidal efficacies were shown in table 11.

TABLE 11

| | Concentration (mg/ml) | | | |
|---|---|---|---|---|
| Polymer name | 2.4000 | 1.2000 | 0.6000 | 0.3000 |
| B3 | + | + | + | − |
| C3 | + | − | − | − |
| B4 | + | + | + | − |
| C4 | + | + | − | − |

+ efficient,
− inefficient

2) *Bacillus coli*: *Bacillus* coli was isolated from chick intestines in the chicken farm, the concentration of bacteria was $2 \times 10^8$ cfu/ml, and the bactericidal efficacies were shown in table 12.

TABLE 12

| | Concentration (mg/ml) | | |
|---|---|---|---|
| Polymer name | 2.4000 | 1.2000 | 0.6000 |
| B3 | + | − | − |
| C3 | − | − | − |
| B4 | + | + | − |
| C4 | − | − | − |

+ efficient,
− inefficient

3) *Bacillus aeruginosus*: *Bacillus aeruginosus* was standard bacteria strain at a concentration of $1.7 \times 10^5$ cfu/ml, and the bactericidal efficacies were shown in table 13.

TABLE 13

| | Concentration (mg/ml) | | |
|---|---|---|---|
| Polymer name | 2.4000 | 1.2000 | 0.6000 |
| B3 | + | − | − |
| C3 | − | − | − |
| B4 | + | + | − |
| C4 | − | − | − |

+ efficient,
− inefficient

4) *Salmonella*: *Salmonella* was isolated from chick intestines in the chicken farm, the concentration of bacteria was $1.9 \times 10^5$ cfu/ml, and the bactericidal efficacies were shown in table 14.

TABLE 14

| | Concentration (mg/ml) | | |
|---|---|---|---|
| Polymer name | 2.4000 | 1.2000 | 0.6000 |
| B3 | + | − | − |
| C3 | − | − | − |
| B4 | + | + | − |
| C4 | + | − | − |

+ efficient,
− inefficient

EXAMPLE 2

Control drug: (acrylic acid:acrolein (mol)=90:10): 7.04 g freshly distilled acrolein and 81.43 g freshly distilled acrylic acid were added into a three-port flask with 530 ml absolute methanol, purged with nitrogen, 5.47 g benzoyl peroxide was added, and the solution was stirred and heated to reflux under nitrogen for 50 h. The reaction solution became a yellowish viscous liquid, which was dried under vacuum at 50-100° C. for 24 hours to form poly (acrolein-acrylic acid) named A5.

Invented drug (acrylic acid:acrolein:fumaric acid (mol)= 85:10:5): 8.05 g freshly distilled acrolein, 87.91 g freshly distilled acrylic acid and 8.34 g fumaric acid were added into a three-port flask with 570 ml absolute methanol, purged with nitrogen, 5.18 g benzoyl peroxide was added, and the solution was stirred and heated to reflux under nitrogen for 50 h. The reaction solution became a yellowish viscous liquid, which was dried under vacuum at 50-100° C. for 24 hours to form poly (acrolein, acrylic acid, fumaric acid) named A6.

Contrast Experiments of Dissolubility:
The results were shown in table 15.

TABLE 15

| Name | | Boiling without sodium carbonate Phenomena | PH | added sodium carbonate Phenomena | Adjust PH to | Adjust PH to |
|---|---|---|---|---|---|---|
| Poly (acrolein, acrylic acid) | A5 | Turbid solution after boiling | 2.15 | Transparent solution | 4.12 (B5) | 8.36 (C5) |
| Poly (acrolein, acrylic acid, fumaric acid) | A6 | Basically transparent solution after boiling | 2.18 | Transparent solution | 4.10 (B6) | 8.28 (C6) |

Contrast Experiments of Toxicity:
The results were shown in table 16:

TABLE 16

| Polymer name | Dose (mg/kg body weight) | Number of dead rats |
|---|---|---|
| Poly (acrolein, acrylic acid) A5 | 5000 | 0 |
| | 10000 | 1 |
| Poly (acrolein, acrylic acid, fumaric acid) A6 | 5000 | 1 |
| | 10000 | 1 |

Contrast Experiments of Bactericidal Efficacy:

1) *Staphylococcus aureus*: *Staphylococcus aureus* was isolated from chick intestines in the chicken farm, the concentration of bacteria was $5.0 \times 10^7$ cfu/ml, and the bactericidal efficacies were shown in table 17.

TABLE 17

| Polymer name | Concentration (mg/ml) | | | |
|---|---|---|---|---|
| | 2.4000 | 1.2000 | 0.6000 | 0.3000 |
| B5 | + | − | − | − |
| C5 | − | − | − | − |
| B6 | + | + | + | − |
| C6 | + | − | − | − |

+ efficient,
− inefficient

2) *Bacillus coli*: *Bacillus coli* was isolated from chick intestines in the chicken farm, the concentration of bacteria was $3.5 \times 10^7$ cfu/ml, and the bactericidal efficacies were shown in table 18.

TABLE 18

| Polymer name | Concentration (mg/ml) | | | |
|---|---|---|---|---|
| | 2.4000 | 1.2000 | 0.6000 | 0.3000 |
| B5 | + | + | − | − |
| C5 | + | − | − | − |
| B6 | + | + | + | − |
| C6 | + | − | − | − |

+ efficient,
− inefficient

3) *Bacillus aeruginosus*: *Bacillus aeruginosus* was standard bacteria strain at a concentration of $2.8 \times 10^5$ cfu/ml, and the bactericidal efficacies were shown in table 19.

TABLE 19

| Polymer name | Concentration (mg/ml) | | |
|---|---|---|---|
| | 2.4000 | 1.2000 | 0.6000 |
| B5 | + | + | − |
| C5 | − | − | − |
| B6 | + | + | − |
| C6 | + | − | − |

+ efficient,
− inefficient

4) *Salmonella*: Salmonellae was isolated from chick intestines in the chicken farm, the concentration of bacteria was $2.1 \times 10^5$ cfu/ml, and the bactericidal efficacies were shown in table 20.

TABLE 20

| Polymer name | Concentration (mg/ml) | | |
|---|---|---|---|
| | 2.4000 | 1.2000 | 0.6000 |
| B5 | + | + | − |
| C5 | + | − | − |
| B6 | + | + | − |
| C6 | + | + | − |

+ efficient,
− inefficient

EXAMPLE 3

Control drug: (acrylic acid:acrolein (mol)=80:20): 39.15 g freshly distilled acrolein and 201.24 g freshly distilled acrylic acid were added into a three-port flask with 600 ml absolute methanol, purged with nitrogen, 12.78 g benzoyl peroxide was added, and the solution was stirred and heated to reflux under nitrogen for 60 h. The reaction solution became a yellow viscous liquid, which was dried under vacuum at 50-100° C. for 24 hours to form poly (acrolein, acrylic acid) named A7.

Invented drug (acrylic acid:acrolein:fumaric acid (mol)=72:20:8): 42.99 g freshly distilled acrolein, 198.9 g freshly distilled acrylic acid and 35.58 g fumaric acid were added into a three-port flask with 570 ml absolute methanol, purged with nitrogen, 11.73 g benzoyl peroxide was added, and the solution was stirred and heated to reflux under nitrogen for 60 h. The reaction solution became a yellow viscous liquid, which was dried under vacuum at 50-100° C. for 24 hours to form Poly (acrolein, acrylic acid, fumaric acid) named A8.

Contrast Experiments of Dissolubility:
The results were shown in table 21.

TABLE 21

| Name | | Boiling without sodium carbonate Phenomena | PH | added sodium carbonate Phenomena | Adjust PH to | Adjust PH to |
|---|---|---|---|---|---|---|
| Poly (acrolein, acrylic acid) | A7 | small jelly after boiling for 24 h | | transparent solution after boiling for 12 h | 4.02 (B7) | 8.10 (C7) |
| Poly (acrolein, acrylic acid, fumaric acid) | A8 | Milky solution after boiling for 10 min | 2.16 | Transparent solution | 4.00 (B8) | 8.12 (C8) |

Contrast Experiments of Toxicity:

The results were shown in table 22:

TABLE 22

| Polymer name | Dose (mg/kg body weight) | Number of dead rats |
| --- | --- | --- |
| Poly (acrolein, acrylic acid) A7 | 5000 | 1 |
| | 10000 | 2 |
| Poly (acrolein, acrylic acid, fumaric acid) A8 | 5000 | 0 |
| | 10000 | 2 |

Contrast Experiments of Bactericidal Efficacy:

1) *Staphylococcus aureus*: *Staphylococcus aureus* was isolated from chick intestines in the chicken farm, the concentration of bacteria was $5.8 \times 10^6$ cfu/ml, and the bactericidal efficacies were shown in table 23.

TABLE 23

| Polymer name | Concentration (mg/ml) | | | |
| --- | --- | --- | --- | --- |
| | 2.4000 | 1.2000 | 0.6000 | 0.3000 |
| B7 | + | + | − | − |
| C7 | + | − | − | − |
| B8 | + | + | + | − |
| C8 | + | − | − | − |

+ efficient,
− inefficient

2) *Bacillus coli*: *Bacillus coli* was isolated from chick intestines in the chicken farm, the concentration of bacteria was $2.0 \times 10^7$ cfu/ml, and the bactericidal efficacies were shown in table 24.

TABLE 24

| Polymer name | Concentration (mg/ml) | | | |
| --- | --- | --- | --- | --- |
| | 2.4000 | 1.2000 | 0.6000 | 0.3000 |
| B7 | + | − | − | − |
| C7 | + | − | − | − |
| B8 | + | + | + | − |
| C8 | + | − | − | − |

+ efficient,
− inefficient

3) *Bacillus aeruginosus*: *Bacillus aeruginosus* was standard bacterial strain at a concentration of $2.0 \times 10^5$ cfu/ml, and the bactericidal efficacies were shown in table 25.

TABLE 25

| Polymer name | Concentration (mg/ml) | | | |
| --- | --- | --- | --- | --- |
| | 2.4000 | 1.2000 | 0.6000 | 0.3000 |
| B7 | + | − | − | − |
| C7 | − | − | − | − |
| B8 | + | + | + | − |
| C8 | + | − | − | − |

+ efficient,
− inefficient

4) *Salmonella*: *Salmonella* was isolated from chick intestines in the chicken farm, the concentration of bacteria was $9.1 \times 10^4$ cfu/ml, and the bactericidal efficacies were shown in table 26.

TABLE 26

| Polymer name | Concentration (mg/ml) | | | |
| --- | --- | --- | --- | --- |
| | 2.4000 | 1.2000 | 0.6000 | 0.3000 |
| B7 | + | + | − | − |
| C7 | + | − | − | − |
| B8 | + | + | + | − |
| C8 | + | + | − | − |

+ efficient,
− inefficient

EXAMPLE 4

Control drug: (acrylic acid:acrolein (mol)=75:25): 47.64 g freshly distilled acrolein and 183.75 g freshly distilled acrylic acid were added into a three-port flask with 540 ml absolute methanol, purged with nitrogen, 11.43 g benzoyl peroxide was added, and the solution was stirred and heated to reflux under nitrogen for 65 h. The reaction solution became a yellow viscous liquid, which was dried under vacuum at 50-100° C. for 24 hours to form poly (acrolein, acrylic acid) named A9.

Invented drug (acrylic acid:acrolein:fumaric acid (mol)= 65:25:10): 56.91 g freshly distilled acrolein, 190.23 g freshly distilled acrylic acid and 47.13 g fumaric acid were added into a three-port flask with 570 ml absolute methanol, purged with nitrogen, 12.30 g benzoyl peroxide was added, and the solution was stirred and heated to reflux under nitrogen for 65 h. The reaction solution became a yellow viscous liquid, which was dried under vacuum at 50-100° C. for 24 hours to form Poly (acrolein, acrylic acid, fumaric acid) named A10.

Contrast Experiments of Dissolubility:

The results were shown in table 27.

TABLE 27

| Name | | Boiling without sodium carbonate | | added sodium carbonate | |
| --- | --- | --- | --- | --- | --- |
| | | Phenomena | PH | Phenomena | Adjust PH to | Adjust PH to |
| Poly (acrolein, acrylic acid) | A9 | Only swelling after boiling for 24 h | | transparent solution after boiling for 20 h | 4.22 (B9) | 8.16 (C10) |
| Poly (acrolein, acrylic acid, fumaric acid) | A10 | Turbid solution after boiling for 1 h | 2.22 | transparent sodium | 4.25 (B10) | 8.18 (C10) |

Contrast Experiments of Toxicity:

The results were shown in table 28:

TABLE 28

| polymer name | Dose (mg/kg body weight) | Number of dead rats |
|---|---|---|
| Poly (acrolein, acrylic acid) A9 | 5000 | 1 |
| | 10000 | 3 |
| Poly (acrolein, acrylic acid, fumaric acid) A10 | 5000 | 1 |
| | 10000 | 4 |

Contrast Experiment of Bactericidal Efficacy:

1) *Staphylococcus aureus*: *Staphylococcus aureus* was isolated from chick intestines in the chicken farm, the concentration of bacteria was $8.2 \times 10^6$ cfu/ml, and the bactericidal efficacies were shown in table 29.

TABLE 29

| Polymer name | Concentration (mg/ml) | | | |
|---|---|---|---|---|
| | 2.4000 | 1.2000 | 0.6000 | 0.3000 |
| B9 | + | + | + | − |
| C9 | + | − | − | − |
| B10 | + | + | + | − |
| C10 | + | + | − | − |

+ efficient,
− inefficient

2) *Bacillus coli*: *Bacillus coli* was isolated from chick intestines in the chicken farm, the concentration of bacteria was $8.4 \times 10^6$ cfu/ml, and the bactericidal efficacies were shown in table 30.

TABLE 30

| Polymer name | Concentration (mg/ml) | | |
|---|---|---|---|
| | 2.4000 | 1.2000 | 0.6000 |
| B9 | + | − | − |
| C9 | − | − | − |
| B10 | + | + | − |
| C10 | − | − | − |

+ efficient,
− inefficient

3) *Bacillus aeruginosus*: *Bacillus aeruginosus* was standard bacterial strain at a concentration of $1.3 \times 10^6$ cfu/ml, and the bactericidal efficacies were shown in table 31.

TABLE 31

| Polymer name | Concentration (mg/ml) | | |
|---|---|---|---|
| | 2.4000 | 1.2000 | 0.6000 |
| B9 | + | − | − |
| C9 | + | − | − |
| B10 | + | + | − |
| C10 | + | − | − |

+ efficient,
− inefficient

4) *Salmonella*: *Salmonella* was isolated from chick intestines in the chicken farm, the concentration of bacteria was $3.3 \times 10^5$ cfu/ml, and the bactericidal efficacies were shown in table 32.

TABLE 32

| Polymer name | Concentration (mg/ml) | | |
|---|---|---|---|
| | 2.4000 | 1.2000 | 0.6000 |
| B9 | + | − | − |
| C9 | − | − | − |
| B10 | + | + | − |
| C10 | + | − | − |

+ efficient,
− inefficient

EXAMPLE 5

Control drug (acrolein:acrylic acid (mol)=65:35): 69.72 g freshly distilled acrolein and 166.44 g freshly distilled acrylic acid were added into a three-port flask with 500 ml absolute methanol, purged with nitrogen, 10.98 g benzoyl peroxide was added, and the solution was stirred and heated to reflux under nitrogen for 75 h. The reaction solution became a dark brown viscous liquid, which was dried under vacuum at 50-100° C. for 24 hours to form poly (acrolein, acrylic acid) named A11.

The invented drug (acrylic acid:acrolein:fumaric acid (mol)=55:35:10): 78.12 g freshly distilled acrolein, 150.80 g freshly distilled acrylic acid and 46.23 g fumaric acid were added into a three-port flask with 590 ml absolute methanol, purged with nitrogen, 9.48 g benzoyl peroxide was added, and the solution was stirred and heated to reflux under nitrogen for 75 h., The reaction solution became a dark brown viscous liquid, which was dried under vacuum at 50-100° C. for 24 hours to form Poly (acrolein, acrylic acid, fumaric acid) named A12.

Contrast Experiment of Dissolubility:

The results were shown in table 33.

TABLE 33

| Name | | Boiling without sodium carbonate | | added sodium carbonate | | |
|---|---|---|---|---|---|---|
| | | Phenomena | PH | Phenomena | Adjust PH to | Adjust PH to |
| Poly (acrolein, acrylic acid) | A11 | Only swelling after boiling for 24 h | | turbid solution after boiling for 48 h | 4.26 (B11) | 8.30 (C11) |
| Poly (acrolein, acrylic acid, fumaric acid) | A12 | turbid solution after boiling | 2.28 | Transparent solution after boiling for 2 hours | 4.18 (B12) | 8.24 (C12) |

Contrast Experiment of Toxicity:
The results were shown in table 34:

TABLE 34

| Polymer name | Dose (mg/kg body weight) | Number of dead rats |
|---|---|---|
| Poly (acrolein, acrylic acid) A11 | 5000 | 1 |
| | 6500 | 1 |
| | 8000 | 4 |
| | 10000 | 8 |
| Poly (acrolein, acrylic acid, fumaric acid) A12 | 5000 | 1 |
| | 6500 | 2 |
| | 8000 | 5 |
| | 10000 | 10 |

Contrast Experiment of Bactericidal Efficacy:
Experiment

1) *Staphylococcus aureus*: *Staphylococcus aureus* was isolated from chick intestines in the chicken farm, the concentration of bacteria was $3.2 \times 10^8$ cfu/ml, and the bactericidal efficacies were shown in table 35.

TABLE 35

| Polymer name | Concentration (mg/ml) | | | |
|---|---|---|---|---|
| | 2.4000 | 1.2000 | 0.6000 | 0.3000 |
| B11 | + | + | − | − |
| C11 | + | − | − | − |
| B12 | + | + | + | − |
| C12 | + | + | − | − |

+ efficient,
− inefficient

2) *Bacillus coli*: *Bacillus coli* was isolated from chick intestines in the chicken farm, the concentration of bacteria was $1.6 \times 10^7$ cfu/ml, and the bactericidal efficacies were shown in table 36.

TABLE 36

| Polymer name | Concentration (mg/ml) | | |
|---|---|---|---|
| | 2.4000 | 1.2000 | 0.6000 |
| B11 | + | − | − |
| C11 | − | − | − |
| B12 | + | + | − |
| C12 | − | − | − |

+ efficient,
− inefficient

3) *Bacillus aeruginosus*: *Bacillus aeruginosus* was standard bacterial strain at a concentration of $2.5 \times 10^6$ cfu/ml, and the bactericidal efficacies were shown in table 37.

TABLE 37

| Polymer name | Concentration (mg/ml) | | | |
|---|---|---|---|---|
| | 2.4000 | 1.2000 | 0.6000 | 0.3000 |
| B11 | + | + | − | − |
| C11 | + | − | − | − |
| B12 | + | + | + | − |
| C12 | + | − | − | − |

+ efficient,
− inefficient

4) *Salmonella*: *Salmonella* was isolated from chick intestines in the chicken farm, the concentration of bacteria was $9.2 \times 10^4$ cfu/ml, and the bactericidal efficacies were shown in table 38.

TABLE 38

| Polymer name | Concentration (mg/ml) | | | |
|---|---|---|---|---|
| | 2.4000 | 1.2000 | 0.6000 | 0.3000 |
| B11 | + | − | − | − |
| C11 | − | − | − | − |
| B12 | + | + | + | − |
| C12 | + | − | − | − |

+ efficient,
− inefficient

EXAMPLE 6

Preparation of Poly (Acrolein, Acrylic Acid, Maleic Acid)

Invented drug (acrolein:acrylic acid:trans glutaconic acid (mol)=80:15:5): 29.20 g freshly distilled acrolein, 200.22 g freshly distilled acrylic acid and 20.16 g fumaric acid were added into a three-port flask with 800 ml absolute methanol, purged with nitrogen, 10.55 g benzoyl peroxide was added, and the solution was stirred and heated to reflux under nitrogen for 75 h. The reaction solution became a yellowish viscous liquid, which was dried under vacuum at 50-100° C. for 24 hours to form to Poly (acrolein, acrylic acid, maleic acid) with an average molecular weight no less than 1000.

EXAMPLE 7

The preparation of poly (acrolein, acrylic acid, cis-glutaconic acid) was the same as that in example 1.

EXAMPLE 8

The preparation of poly (acrolein, acrylic acid, and trans-glutaconic acid) was the same as that in example 1.

What is claimed is:

1. A terpolymer comprising repeating units selected from the group consisting of:

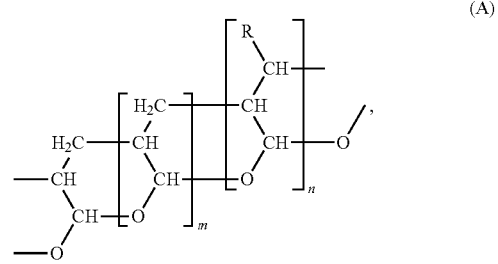

(A)

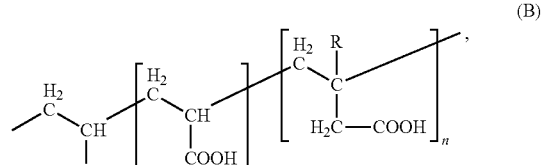

(B)

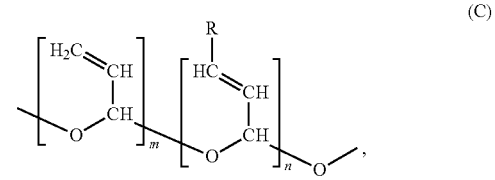

(C)

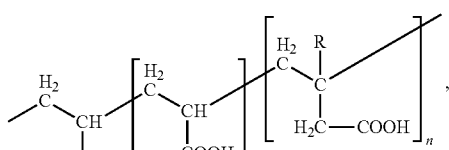

(B)

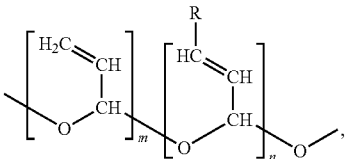

(C)

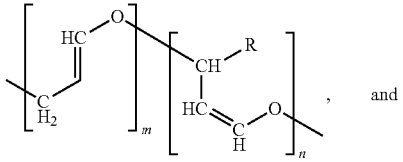

(D)

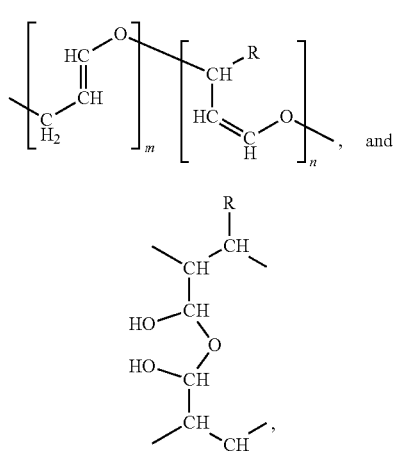

and (E)

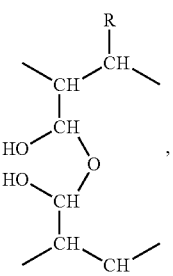

wherein m and n are independently selected from integers equal to or greater than 1, and R is COOH, wherein the polymer has a molecular weight from about 1000 to about 10,000, wherein the repeating units are derived from acrylic acid, acrolein and fumaric acid, wherein the mole ratio of acrylic acid:acrolein:fumaric acid is 55-85:10-35:5-10; wherein said terpolymer is prepared by a method comprising the steps of:

(i) reacting acrylic acid, acrolein and fumaric acid in methanol,
(ii) heating to reflux under nitrogen, and
(iii) drying under vacuum to form the terpolymer.

2. The terpolymer of claim 1, wherein the mole ratio of acrylic acid:acrolein:fumaric acid is 63:30:7.

3. A composition comprising the terpolymer of claim 1.

4. The composition of claim 3, further comprising a pharmaceutically acceptable carrier.

5. The composition of claim 3, wherein the composition is formulated as tablets, capsules, oral liquid, suspensions, pills, granules, ointment, or suppositories.

6. A method of treating microbial infection in a subject, comprising the step of administering to the subject a composition comprising the terpolymer of claim 1.

7. The method of claim 6, wherein the microbial infection is bacterial infection or parasitic infection.

8. The method of claim 6, wherein the subject is an animal or a human.

9. A method of preparing a terpolymer comprising repeating units selected from the group consisting of:

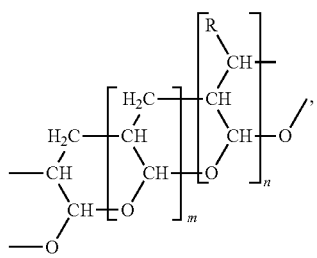

(A)

wherein m and n are independently selected from integers equal to or greater than 1, and R is COOH, wherein the polymer has a molecular weight from about 1000 to about 10,000, wherein the repeating units are derived from acrylic acid, acrolein and fumaric acid, wherein the mole ratio of acrylic acid:acrolein:fumaric acid is 55-85: 10-35:5-10; said method comprising the steps of:

(i) reacting acrylic acid, acrolein, and fumaric acid with methanol;
(ii) heating to reflux under nitrogen; and
(iii) drying under vacuum to form the terpolymer.

10. The method of claim 9, wherein the mole ratio of acrylic acid:acrolein:fumaric acid is 63:30:7.

11. The method of claim 9, wherein the mole ratio of acrylic acid:acrolein:fumaric acid is 85:10:5.

12. The method of claim 9, wherein the mole ratio of acrylic acid:acrolein:fumaric acid is 72:20:8.

13. The method of claim 9, wherein the mole ratio of acrylic acid:acrolein:fumaric acid is 65:25:10.

14. The method of claim 9, wherein the mole ratio of acrylic acid:acrolein:fumaric acid is 55:35:10.

* * * * *